United States Patent
Gonzalez

(12) 
(10) Patent No.: US 6,716,246 B1
(45) Date of Patent: Apr. 6, 2004

(54) PROCESS AND DEVICE FOR FACILITATING THE IMPLANTATION OF BIOLOGICAL MATERIAL

(75) Inventor: Rafael Valdes Gonzalez, Mexico City (MX)

(73) Assignee: Universidad Nacional Autonoma de Mexico, Delegacion Coyoacon (MX)

( * ) Notice: Subject to any disclaimer, the term of this patent is extended or adjusted under 35 U.S.C. 154(b) by 0 days.

(21) Appl. No.: 09/868,103

(22) PCT Filed: Dec. 14, 1999

(86) PCT No.: PCT/MX99/00039
§ 371 (c)(1),
(2), (4) Date: Sep. 19, 2001

(87) PCT Pub. No.: WO00/35371
PCT Pub. Date: Jun. 22, 2000

(30) Foreign Application Priority Data

Dec. 15, 1998 (MX) .............................. 9810667

(51) Int. Cl.[7] .................................................. A61F 2/44
(52) U.S. Cl. .................................................. 623/17.12
(58) Field of Search .............................. 424/422, 423, 424/424; 604/93.01; 623/17.11, 17.12, 17.13–17.16

(56) References Cited

U.S. PATENT DOCUMENTS

| | | | |
|---|---|---|---|
| 5,324,518 A | * 6/1994 | Orth et al. .................. 424/423 |
| 5,569,462 A | 10/1996 | Martinson et al. .......... 424/424 |
| 5,614,205 A | * 3/1997 | Usala .......................... 424/424 |
| 5,725,854 A | * 3/1998 | Selawry ..................... 424/93.7 |

* cited by examiner

Primary Examiner—Corrine McDermott
Assistant Examiner—Hieu Phan
(74) Attorney, Agent, or Firm—Moore & Van Allen PLLC; Michael C. Johnston; Charles L. Evans

(57) ABSTRACT

This invention refers to a device and the procedure for the formation of fibrocollagen tubes that are of use as neovascularized reservoirs to favor the implant of cells and/or substances producing biological factors for the treatment of diseases like diabetes. Similarly, the neovascularized fibrocollagen tube formed is suitable for use, should it so be desired, as splints for the implantation of tissues in surgical operation involving blood vessels, urethra among others.

14 Claims, 3 Drawing Sheets

PROCESS AND DEVICE FOR FACILITATING THE IMPLANTATION OF BIOLOGICAL MATERIAL

DESCRIPTION OF THE INVENTION

1. Technical Field of the Invention

This invention is related to the biomedicine field, particularly with respect to cell implants for the production of biological factors in the treatment of chronic degenerative diseases, such as the generation of material for tissue implants like splints.

2. Background of the Invention

The deficiency of a biological factor in an individual is the main cause of the appearance of chronic degenerative diseases like diabetes mellitus, Parkinson's disease, hypothyroidism and others.

The traditional treatments of some of these diseases have consisted in the application of deficient biological factors in individuals or substances that stimulate their production, generally by means of injections of products obtained from chemistry or biotechnology. This type of treatment has several disadvantages, particularly in relation to the frequency of doses required to maintain the factor at an optimal level, which is virtually impossible to achieve. This, however, continues to be the method that is most frequently used, as it is the easiest and cheapest option available.

In order to improve the bioavailability of the factor, attempts have been made to develop methods, devices and apparatus to control its release.

One alternative refers to pumps that control the dosage of the biological factor, in accordance with its requirement or demand. Apart from being complicated, this method has proved unable to control the dosage as there are no means to measure demand with a certain degree of accuracy and the pumps therefore have not been successful.

Another alternative that has been tried is the implant of cells that produce the biological factor. However, the direct contact of the cells with the patient's body prevents the flow of nutrients with the consequent destruction of cells and so the life of the implanted cells is relatively short and transfer of the biological factors is limited. Consequently, their therapeutic effect is deficient.

The tissues that appear to reject the implants are made up of cells called lymphocytes, plasmatic cells and antibodies. Fibrocollagen is the means to cover foreign bodies, even when they are positive. The amount of fibrocollagen produced is relatively high and it is therefore able to destroy the implanted cells.

These tissues, that are formed in a natural way, could be used in turn as splints for implants in different parts of the body such as blood vessels, urethra, etc, since it is recommendable that said splints come from the patient's own tissues. However, a limiting factor has been found: in order for them to be effective, greater availability in the amount and size of the tissues is required than is available in the body and to date there has not been any method to obtain this type of useful material for use as a splint.

In order to try to avoid the problems of rejection derived from direct cell implant, a variety of devices has been designed that generally consist of a chamber or capsule where cells are placed in such a way that they are isolated and have no contact with the individual's immune system.

The implant devices that contain the cells are generally composed of natural polymers like collagen and alginates or synthetic polymers such as polyacrylates, vinylacrylonitrile, and poly-xylene.

In U.S. Pat. No. 5,614,205, for example, a matrix is described consisting of a poly-para-xylene membrane and a cell culture that produces insulin for the treatment of diabetes mellitus. The membrane has a certain porosity that permits the passage of nutrients and biological factors, but prevents the passage of immune agents. It is mentioned that the biocompatible material does not produce rejection.

In the U.S. Pat. No. 5,569,462 a description is given of how the mortality of cells producing the biological factor of interest occurs because the flows of nutrients and waste products are not adequate during the ischemic period of the implant. The alternative proposal consists in using a device with a chamber for cells where said chamber is immuno-isolated with biocompatible material such as polytetrafluorethylene (PTFE) 15 microns in width and a porosity 5 microns.

Additionally, the uses of immunomodulatory agents such as immuno-suppressive agents like mycophenolic acid, cyclosporin, rapamacyn, etc. or anti-inflammatory agents like corticosteroids are required.

Given that the ischemic period finishes when good neovascularization has been achieved, the inventors propose the use of means for a better neovascularization, such as the use of a substance or cells that promote or produce the substance stimulating neovascularization.

These devices do not satisfactorily solve the various disadvantages of the implants already mentioned because, although they are biocompatible materials, there is still tissue formation and inadequate vascularization around the device in relatively short periods of time after the implant. Hence the flow of blood to the tissues in that region is low and therefore nutrient availability is also low.

Although they are permeable, the device construction materials represent an additional barrier to the exchange of nutrients and biological factors between the implanted cells and the patient's body.

Furthermore, it is well known that the use of products like cyclosporin to reduce the immune response and inhibit the recognition and rejection of transplants and/or implants has negative effects on neovascularization, and therefore the probability is increased of the transplant or implant being unsuccessful.

The U.S. Pat. No. 5,725,854 claims a method for the treatment of diseases that comprises the administration of Sertolli cells, together with cells that produce the biological factor. Here an attempt is made to create an immunologically privileged site. It is well known that Sertolli cells promote immunological tolerance and contain a high amount of elements to protect the cells that produce the biological factor and to maintain their functioning for an indefinite period of time. However, with this alternative rejection is not completely eradicated and it is therefore necessary to continue administering immunosuppressive or immunomodulatory agents which, in turn, have a negative effect on neovascularization.

Furthermore, in none of the previously mentioned inventions is a way established to control the amount of fibrocollagen produced, and it is precisely this substance that is the main factor behind implant rejection.

For this reason, it is still necessary to find an efficacious, efficient way of successfully implanting cells producing biological factors for the treatment of disease.

It is therefore one of the objectives of this invention to provide a procedure for the development of tissues in a conveniently easy and inexpensive way that can be used both to receive the implant of cells producing biological factors for the treatment of diseases and to provide splints that can be used as tissue grafts.

A further objective of this invention is to have the means to form natural fibrocollagen tubes of a controlled width, diameter and length.

Another of the objectives of this invention is to provide an isolated site with characteristics that will permit good neovascularization for the adequate transfer of nutrients and biological factors.

Yet another objective of this invention is to reduce the use of immunomodulatory substances.

These and other objectives will be appreciated in greater detail in the following detailed description of the invention.

In the following description of the invention reference will be made to the drawings in order to give greater clarity to the description.

DETAILED DESCRIPTION OF THE INVENTION

Figure 1:
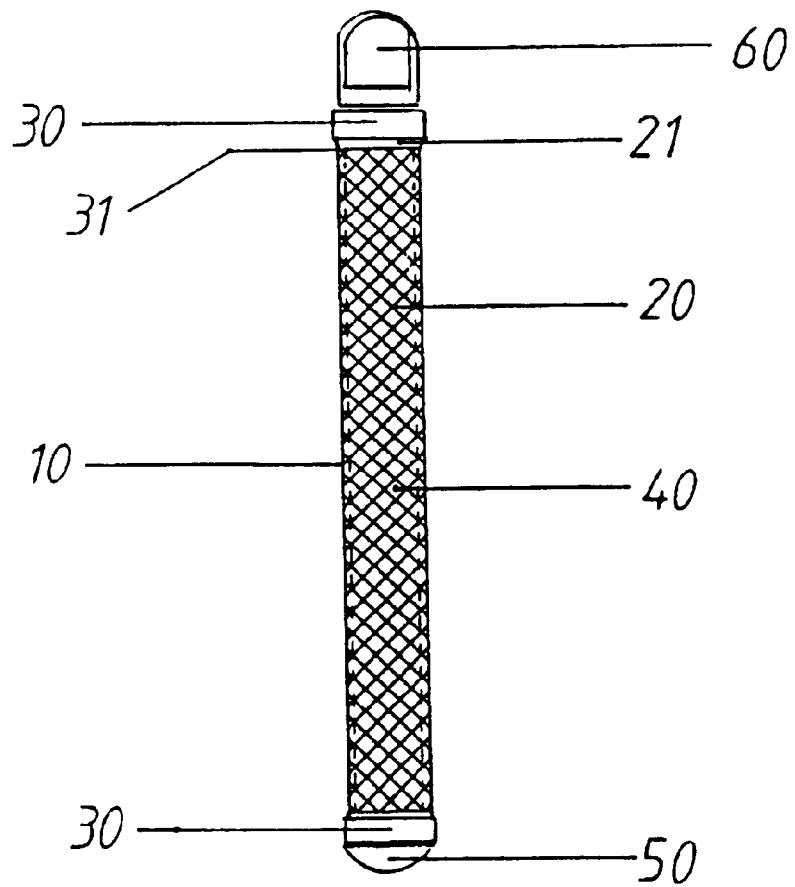
FIG. 1 represents a general and a perspective view of the preferred device to carry out the procedure, both in accordance with the present invention.

In accordance with FIG. 1, this is a device (10) that consists of an intermediate section or body (20), that is preferably porous, and has a cavity inside it that houses a plunger (40), and at whose ends can be found sealing sets or mechanisms (30), one of which connects to the first sealing element (50), while the other connects to the second sealing element (60), one end of which is joined to the plunger (40) in such a way that when the device is closed by means of the second sealing plugs (60), it is kept rigidly in place inside the porous body (20) of said plunger (40). It should be mentioned that, in accordance with the procedure in which the device referred to is used, and in accordance with this invention, the second sealing element (60) may be substituted for by another sealing element (50) or similar element, in such a way that the cavity that houses the plunger (40) remains free and in this way an interior space is generated that is adequate for receiving cells and/or substances of the production of the biological factor in question as can be appreciated throughout the description of this invention.

The porous body (20) is preferably made up of a cylindrical grid, of the type that can be of stainless steel, inert polymer or any other material, which can give dimensional stability to the intermediate part of the set of the device (10) and the necessary porosity inside said device. In accordance with the objectives of this invention, the degree of porosity of the intermediate porous body (20) of the present invention must have a mesh size of 40 to 150 Mesh (square per linear inch), preferably in a cylindrical form. The length of this intermediate porous section or porous body (20) can be any adequate length that accords with therapeutic needs in order to adequately favor the production of the biological factor necessary; that is around 10 to 80 millimeters. However, the length can be considerably longer according to the type of use to which the device will be put, which could, for example, be for obtaining splints, in which case the length would be about 200 millimeters. As already mentioned, both ends of the intermediate porous body of the device described herein are adequately connected to sealing sets (39) and their respective elements (50) and/or (60).

It has been possible to establish that the degree of porosity of the grid that makes up the intermediate porous body (20) determines the size of the neo-formed vessels in the fibrocollagen, in accordance with the procedure put forward herein and the functions of the patient's organism. For this reason, the size of the mesh or pore is determined according to the type of application to which the tube formed from fibrocollagen will be put.

The sealing mechanisms (30) located in the respective ends of the device (10) contemplated in this invention, present a preferably tubular section shape whose length is suitable for the function of sealing both sides of said device and their proportion, with respect to the intermediate porous body (20), can be 10 to 50% of the length and with a diameter similar to that of the porous body (20).

At one end of the sealing mechanisms (30), there are assembly and fastening mechanisms, which in this case can have the preferred form of a female type thread to connect the sealing elements (50) and/or (60). At the opposite end to said sealing mechanisms, there are joining elements (31) that permit the corresponding fastening in the corresponding end of the porous body (20), for which any means, threaded or not, may be used.

In accordance with one of the preferred modalities of the constructive elements of the device of this invention, said joining elements (31) consist preferably of a concentric, grooved element between the internal and external walls of the tube where a portion of one of the ends of the porous body (21) is inserted and fastened to the joint portion of the sealing mechanism (31), in such a way that the pressure of contact between the sealing mechanism and the porous body (21) is greater than the force of tension provoked when the sealing elements (50) and/or (60) are screwed and unscrewed.

Figure 3:
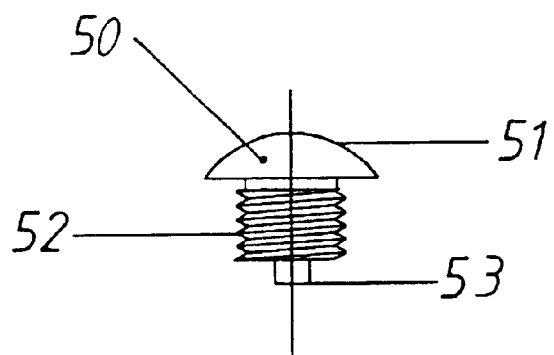
FIG. 3 corresponds to the plunger joined to the sealing mechanism in one of the preferred modalities of this invention.

In accordance with FIG. 3, the set that forms the plunger (40), consists of an element preferably with a solid, cylindrical shaped section, one of the ends of which is connected to the sealing element (60), and is then connected in turn to the corresponding elements of the porous body (20) and the seal (30), respectively. For purposes of identification, sealing element (60) may have a slightly different shape to sealing element (50) in order to identify it with respect to sealing element (50) and remove it in accordance with the procedures for use. At the distal end or the end opposite to the plunger (40), is the finishing piece of said element which may have a groove or joint (41) to be connected to the inside end (53) of the scaling element (50) of the connected set of the device of this invention, in such a way that the plunger (40) is maintained completely fixed within the porous body (20) and the predetermined separation between both elements is concentrically constant. This modality needs the length of said plunger (40) to be practically equal to the length of the set of the porous body (20) with the sealing mechanisms (30). It should be mentioned that the information given here covers the modality in which the plunger (40) is long enough to permit its end (41) having contact with and connecting itself to the corresponding sealing element (50) mechanism (53). However, good results can also be achieved with a plunger whose length is only part of the length of the porous body. The diameter of the plunger

(40) can be virtually the equivalent of the interior diameter of the porous body (20). However, for better results it is preferable to have a distance between the interior diameter of the porous body with respect to the exterior diameter of the plunger of 1 to 10 millimeters, with the diameter of the plunger being preferably 4 to 25 millimeters.

The plunger can be solid or hollow. The applicant has found, however, that the use of a hollow plunger has serious disadvantages since when the device is placed in the patient's body liquid is trapped in the hollow space in the plunger and decomposes over time and could lead to possible infections.

Figure 2:
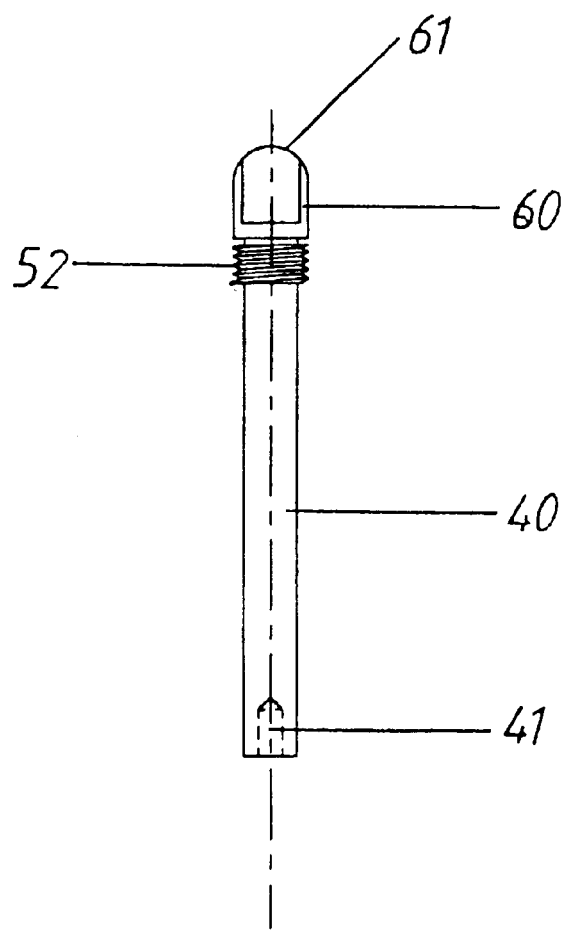
FIG. 2 corresponds to one of the preferred modalities of one of the sealing plugs of the device contemplated in this invention.

In accordance with FIG. 2, the sealing element (50) may have a conventional shape. However, in a preferred modality for a better performance of this invention, said sealing element includes a fastening zone (51), defined by a head with a preferably semi-spherical shape; a cylindrical zone of union with a fastening mechanism corresponding to the sealing mechanism (30) of the porous body (20) that may be of the male type of thread (52), with a diameter preferably similar to those of the sealing mechanisms (30) in order to be adequately joined to them; and a concentric fastening zone consisting of a cylindrical element with a preferred diameter of 1 to 4 millimeters, but smaller than the hole of the fastening section (41) of the plunger (40), which is an alignment guide for the plunger in the connected set of the device of this invention.

For the purpose of easily connecting and disconnecting (preferably screwing and unscrewing) the sealing elements (50) and/or (60), the semi-spherical head of the fastening zone (51) has a hole that can be of any geometrical shape that facilitates the use of an appropriate tool as may be, for example, the use of a tool like some kind of wrench, Allen wrench or some other kind.

In the preferred modality of this invention, the fastening zone (52) of the sealing element (60) and the fastening section (41) of the plunger (40) form a one piece set so that manipulation of both elements is easier. This one piece set contains the fastening zone (61), and an additional support section comprising an elongated element with two side faces parallel and perpendicular to the axis of the sealing plug (60) over 50% of its length in order to form a support set for the thumb and index finger when screwing and unscrewing the set within the female threading section of the sealing mechanisms (30). The length of said support section can be 10 to 40% the length of the porous body (20).

Once in use, the thickness of the fibrocollagen tube generated depends on the separation between the porous body (20) and the plunger (40) and thus separation is determined according to the requirements arising from the use of the fibrocollagen tube. Said separation defines the resistance to collapse of the tube and the uniformity of the fibrocollagen bed.

The diameters of the porous body (20) and the plunger (40) are chosen in accordance with the volume and thickness required, from 4 to 35 millimeters, with separation or a beam of light from 1 to 10 millimeters.

The applicant has found that the thickness of the fibrocollagen tube and the size of the neo-formed vessels are important characteristics that provide a site with optimal conditions for the survival of the cells for periods that are adequate for the maintenance of an effective therapeutic effect.

The device is manufactured with materials of a medical degree. For example, these materials can be stainless steel, virgin polytetrafluororethylene (PTFE), titanium, etc.

As can be deduced from the description of the device to favor the implant of biological material, the pieces can be made by machining the threaded parts or by injection into molds. The process chosen depends on the materials that will be used.

In accordance with this invention, the procedure for the implantation of biological material, in its modality as reservoir resulting from the formation of a biological fibrocollagen tube making use of the previously mentioned device, consists of: the implantation of the device set in the body of the patient or individual, with the sealing element (60) placed at one of the ends of the porous body in such a way that the plunger (40) is incorporated inside it. When implanted in this way, the porous body (20) is overlain with fibrocollagen by the natural action of the patient's body. Subsequently, once the fibrocollagen layer has been formed, a partial incision is made in order to expose the part of the device that has the sealing element joined to the plunger (60) in order to remove it. When said plunger is removed, a neovascularized fibrocollagen tube can be found that is suitable for implantation of biological factor producing cells through the hole in the sealing element (60). The device is closed now with a sealing element (50) in such a way that the fibrocollagen tube is closed within the organism. In these terms, the biological factor promoter cells act in contact with the neo-formed, vascularized tissues and the biological factor is absorbed by the blood stream.

In another modality of using the device, in order for the fibrocollagen tube generated inside the individual's organism to be a kind of agent generating tissues for implants, in accordance with the procedure described above, said tube can be removed with no need to disconnect the sealing element and the plunger (60), but by completely removing the device set and fibrocollagen tube from the patient's or individual's body and said tissues are capable of and suitable to be used as tissue implants or splints. If necessary, the sealing elements (50) and (60) and the plunger (40) are removed; the fibrocollagen tube is then ready to be immediately implanted in the required place or used as is intended.

When used as promoter of fibrocollagen tubes, the diameter of the device can be from 4 to 25 millimeters of light and the length is determined by calculations, based on the necessities of shape, when it is used as a splint.

When it is used as a reservoir of biological material, only one of the sealing elements (60) is removed with the plunger (40), or the set formed by both elements. The biological material, made up of the biological factor producing cells, and optionally a culture medium within the fibrocollagen tube are injected in the space left empty by the plunger (40) and a sealing element (50) is installed to avoid the biological material reaching places where the fibrocollagen tube has not been formed.

In order to increase the effectiveness of the treatment, factor producing cells that have been genetically manipulated by known techniques can be used.

The culture medium that is optionally used is selected in accordance with the type of cell to be implanted.

The applicant has found that with the use of the device contemplated in this invention, it has been possible to obtain semi-isolated sites with good neovascularization and conditions therefore exist for cell viability. Similarly, a good interchange rate of biological factors is obtained. For example, in the treatment of diabetes, a better response can be observed to the stimulus provided by the level of glucose in the blood.

The amount of cells, for the case of the treatment of diabetes referred to in the literature, is 6,000 to 1,000 islets of Langerhans per kilogram of the patient's weight. In the case of this invention, it has been seen that these can be combined with Sertolli cells in order to immunologically protect them from rejection. However, in addition to the above, the device can be used to place inside it cells that produce substances with a therapeutic activity, as is the case of thyroid and parathyroid cells, among others, without this meaning that the device has effects not included in the spirit of this invention.

EXAMPLES OF APPLICATIONS

The device contemplated in this invention was implanted in its preferred modality in order to favor the implant of cells promoting a biological factor in the dorsal part of a sample of Long Evans rats weighing between 180 and 200 grams.

Diabetes was induced by means of an intravenous application of 65 mg/kg of streptozotocin to the group of ten rats with the device, object of this invention, and a control group.

The level of glucose in both groups showed no important differences, being in the order of 337 mg/dL.

A transplant of islets of Langerhans was performed with both groups and the islets were isolated and conserved using known conventional techniques with the difference that the group of rats with the device received the islets of Langerhans in the site formed by the device. None of the animals were administered immunodepressive agents.

Glucose levels were measured daily during the first week and subsequently once a week.

The animals in the control group showed glycemia of over 250 mg/dL during two consecutive days in the first three days.

The animals with the device to promote fibrocollagen tubes showed a significant decrease in glucose levels to 150 mg/dL.

Having described the invention, the following is claimed:

1. A device for the implantation of biological material comprising:
   a central porous tubular body;
   sealing mechanisms in the corresponding ends of said porous body;
   a plunger; and
   sealing elements for the body of the device.

2. A device for the implantation of biological material, in accordance with claim 1, wherein the central porous body is based on a grid with a cylindrical shape, with mesh the size of 40 to 150 mesh and a diameter of 5 to 35 millimeters.

3. A device for the implantation of biological material, in accordance with claim 1, wherein the porous body contains sealing mechanisms in its ends which also have threaded connecting mechanisms, of the female type for its assembly.

4. A device for the implantation of biological material, in accordance with claim 1, wherein the plunger consists of a cylindrical element with a diameter preferably of 4 to 25 millimeters.

5. A device for the implantation of biological material, in accordance with claim 1, wherein the sealing elements consist of a fastening sequin; a cylindrical joining section with a male type thread; and a concentric fastening section 1 to 5 millimeters in diameter.

6. A device for the implantation of biological material, in accordance with claim 1, wherein the plunger is joined to or forms part of at least one of the sealing elements.

7. A device for the implantation of biological material, in accordance with claim 1, wherein the device is made of material that can be sterilized.

8. A device for the implantation of biological material, in accordance with claim 1, wherein the space between the plunger and the porous body varies in accordance with the thickness of the desired fibrocollagen tube from 1 to 15 millimeters.

9. A process for the implantation of biological material, comprising the steps of:
   implanting in the patient or individual a device to implant biological material;
   observing the formation or deposit of fibrocollagen around said device until a reservoir or tube of neovascularized fibrocollagen is formed; and
   implanting, inside the reservoir or tube of neovascularized fibrocollagen, cells and/or reagents producing the biological factor desired.

10. A process for the implantation of biological material, in accordance with claim 9, wherein the substance producing biological factors is a culture of live cells.

11. A process for the implantation of biological material, in accordance with claim 10, wherein the substance producing biological factors contains Sertolli cells.

12. A process for the implantation of biological material, in accordance with claim 10, wherein the live cells are islets of Langerhans.

13. A process and device for the implantation of biological material, in accordance claim 9, wherein removing the plunger inside the device once said tube or reservoir of neovascularized fibrocollagen has been formed; implanting the substance producing the biological factor desired; closing the tube or reservoir of neovascularized fibrocollagen with an element that will permit the existence of a space within said tube or reservoir of neovascularized fibrocollagen.

14. A process and device for the implantation of biological material, in accordance with claim 13, wherein the fibrocollagen tube that is formed can be used as a graft, preferably vascular, of the trachea, urethra or esophagus among others.

* * * * *